United States Patent [19]

Demole et al.

[11] Patent Number: 5,354,735

[45] Date of Patent: Oct. 11, 1994

[54] USE OF A CYCLOPENTADECENONE AS PERFUMING INGREDIENT

[75] Inventors: Edouard Demole, Coppet; Cyril Mahaim, Echichens; Pierre-Alain Blanc, Crassier, all of Switzerland

[73] Assignee: Firmenich SA, Geneva, Switzerland

[21] Appl. No.: 82,214

[22] Filed: Jun. 24, 1993

[30] Foreign Application Priority Data

Jul. 30, 1992 [CH] Switzerland ............ 2395/92

[51] Int. Cl.$^5$ .................................. A61K 7/46
[52] U.S. Cl. .................... 512/8; 252/174.11; 252/8.6; 424/76.4
[58] Field of Search ............ 512/8; 252/174.11, 86; 424/76.4

[56] References Cited

U.S. PATENT DOCUMENTS

| | | | |
|---|---|---|---|
| 3,778,483 | 12/1973 | Becker et al. | 512/8 |
| 4,346,023 | 8/1982 | Buchi et al. | 512/8 |
| 4,480,107 | 10/1984 | Schulte-Elte et al. | 549/355 |

FOREIGN PATENT DOCUMENTS

| | | | |
|---|---|---|---|
| 0025869A1 | 8/1980 | European Pat. Off. | C07C 49/58 |
| 1558413 | 8/1967 | France | 512/8 |
| 52-42787 | 10/1977 | Japan | 512/8 |
| 55-12408 | 4/1980 | Japan | 512/8 |
| 2058786 | 4/1981 | United Kingdom | 562/8 |

OTHER PUBLICATIONS

S. Arctander, *Perfume and Flavor Chemicals*, Sections 1214, 1985, 2278, 2279 (1969).

*Primary Examiner*—James H. Reamer
*Attorney, Agent, or Firm*—Pennie & Edmonds

[57] ABSTRACT

3-Methyl-cyclopentadec-5-en-1-one and its cis- and transconfiguration isomers are useful as perfuming ingredients, for the preparation of perfuming compositions and perfumed articles to which they impart musky notes characteristic of nitro-musks.

14 Claims, No Drawings

USE OF A CYCLOPENTADECENONE AS PERFUMING INGREDIENT

BRIEF SUMMARY OF THE INVENTION

The present invention relates to the field of perfumery. It concerns, more particularly, a method to confer, improve, enhance or modify the odor properties of a perfuming composition or a perfumed article, which method comprises adding to said composition or article a fragrance effective amount of 3-methyl-cyclopentadec-5-en-1-one.

The invention also concerns a perfuming composition or a perfumed article containing 3-methyl-cyclopentadec-5-en-1-one as active perfuming ingredient.

Another object of the invention is a composition containing 3-methyl-cyclopentadec-5-en-1-one and 3-methyl-cyclopentadec-4-en-1-one, and wherein the weight proportion of 3-methyl-cyclopentadec-5-en-1-one is equal to 70% or more.

The invention further provides a method of use of this latter composition in perfumery.

BACKGROUND OF THE INVENTION

3-Methyl-cyclopentadec-5-en-1-one is a macrocyclic ketone and an unsaturated homolog of muscone, a compound which is well appreciated in perfumery. Owing to the presence of a ring double bond, there are several possible position and configuration isomers for this molecule. The structure of some of them is known. Thus, the structure of the above-mentioned enone, as well as that of several of its isomers, has been described in the literature, mostly in connection with organic syntheses, namely that of muscone. However, there has been no mention of any possible useful odor properties for these compounds.

An exception is, however, patent U.S. Pat. No. 3,778,483 which describes a process for the preparation of muscone from unsaturated ketones of formula

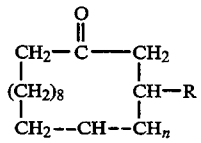
(I)

having a double bond of cis- or trans-configuration in one of the positions indicated by the dotted lines and wherein R represents hydrogen or a methyl radical, one of the n indexes has the value 1 and the other the value 2. The ketones of formula (I) are said to possess a stronger odor than that of their corresponding saturated homolog ketones. According to the inventors of the cited patent, the saturated ketones have a characteristic musky odor, while ketones (I) wherein R is hydrogen possess an odor reminiscent of that of civettone and those wherein R is a methyl have rather a woody odor.

In spite of the fact that several ketones (I), or mixtures of ketones (I), are cited in said patent, namely 3-methyl-cis-cyclopentadec-4-en-1-one (example 4) and 3-methyl-trans-cyclopentadec-4-en-1-one (example 17), as well as a mixture containing essentially the trans isomers of 3-methyl-cyclopentadec-4 and 5-en-1-one (examples 1 et 2), we were unable to find any description of the individual properties of any of these ketones or mixtures, or of the possible olfactive differences between them.

On the other hand, a more recent patent, i.e. GB 2 058 786, reports the preparation of unsaturated macrocyclic ketones of formula

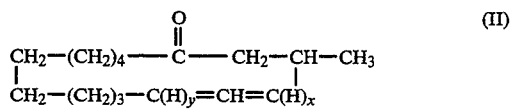

wherein the dotted lines designate the location of a single or double bond and wherein x=1 and y=2, or x=2 and y=1. Although the usefulness of the odor properties of ketones (II) is cited (see page 4, line 18), this citation is based on the above-mentioned prior art and no further description of the properties of 3-methyl-cyclopentadec-4-en-1-one, described in example 5 and designated under the name of "muscenone", can be found in this document.

Finally, a textbook in perfumery, i.e. the book by S. Arctander, Perfume and Flavor Chemicals, Montclair, N.J., USA (1969), describes 3-methyl-cyclopentadecenone under section 1985, also designating it as "muscenone", to which is assigned the structure

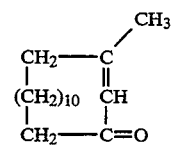

and the odor of which is said to be a "delicate, but extremely tenacious musky odor, upon dilution developing more woody notes, not quite as soft and velvety as those of the muscone, perhaps equal in power, but inferior in beauty" (sic). Curiously, the author also states that "it is inconceivable that this ketone will become a common musk at all" (sic).

Combined with a total lack of analytical characterization of the described compounds, which does not allow a precise teaching of the nature of the compounds and mixtures obtained according to the prior art, these poorly detailed and even somewhat contradictory olfactive descriptions, which moreover are not even supported by examples of perfumery applications, simply suggest that all unsaturated ketones of formula (I) or (II), homologs of muscone and Exaltone ® (cyclopentadecanone; origin: Firmenich SA) possess similar odors, independently of the position or configuration of the double bond.

Yet we have now unexpectedly discovered that this is not at all the case and that, while all the ketones of formula (II) are indeed fragrant substances, their olfactive properties are quite distinct from one to the other, one of these ketones possessing particularly useful and unexpected properties.

THE INVENTION

We have in fact ascertained that 3-methyl-cyclopentadec-5-en-1-one possesses a very musky, slightly animal note, with a strong nitro-musk character, in spite of the absence of nitrogen in the molecule. This odor note is particularly useful because it is known that the use of the nitro-compounds with a musky character is subjected to increasing restrictions for innocuousness and environmental reasons. In view of the prior art discussed above, the character and utility of this note appears as totally unexpected.

Furthermore, we have also established that the two configuration isomers of 3-methyl-cyclopentadec-5-en-1-one possess distinct odors, the cis isomer being preferred for its stronger note, muskier and more elegant but less animal than that of the trans isomer, the latter combining the nitro-musk character with a more marked ambrette seeds note. In both cases, these are odor notes which have been shown to be very tenacious, both on smelling strip and on fabric, the odor of the cis isomer being still more tenacious than that of the trans isomer.

It is quite clear that if the novel and surprising properties of 3-methyl-cyclopentadec-5-en-1-one, and in particular those of its cis isomer, went quite unnoticed in the prior art, it is as a result of the fact that the prior known compounds had not been obtained in a pure state. In actual fact, these compounds are not specifically described in patents U.S. Pat. No. 3,778,483 and GB 2 058 786, even if the given general formulaes appear to include them. The U.S. patent describes either mixtures of isomers, containing both 3-methyl-cyclopentadec-5-en-1-one and 3-methyl-cyclopentadec-4-en-1-one, or the cis isomer of the latter, while patent GB 2 058 786 only describes the preparation of 3-methyl-cyclopentadec-4-en-1-one without specifying any isomeric proportions.

Now, we have discovered that the latter enone develops an odor whose musky character is relatively weak, its cis isomer being almost odorless, while its trans isomer possesses a weak musky note, devoid of character. These three compounds possess odors which are totally devoid of the nitro-musk character which renders 3-methyl-cyclopentadec-5-en-1-one and its isomers so useful. This remarkable difference between the odors of the 3-methylcyclopentadecenone position isomers 4 and 5 shows once again, if needs be, the unpredictable character of all discoveries in the perfumery field, where a slight molecular change can bring about modifications in the olfactive note of a given compound which are sometimes fundamental.

The prior art documents would have led the man in the art to the conclusion that all the unsaturated ketones homolog of muscone and Exaltone ® would be expected to possess similar odors, more woody than musky; they certainly could not have suggested to him that one of these ketones in particular, 3-methyl-cyclopentadec-5-en-1-one, as well as its configuration isomers, would possess novel and surprising odor properties, reminiscent of the odors of the so-called nitro-musks known under the names of "musk ketone" and "musk ambrette" (see S. Arctander, op. cit., sects. 2279 et 2278 respectively). The present invention is based precisely on this discovery and it is thus one of its objects to provide a method of use in perfumery of 3-methyl-cyclopentadec-5-en-1-one and its cis and trans isomers, such as defined above.

As a result of their odor properties, 3-methyl-cyclopentadec-5-en-1-one, and its cis and trans isomers, are equally convenient for fine perfumery and technical perfumery applications. Their tenacity on textiles renders them particularly useful for perfuming laundry detergents and fabric softeners. In these applications, they can be used on their own or in admixture with other perfuming ingredients, solvents or adjuvants of current use in the art. In particular, we have been able to establish that the mixtures of 3-methyl-cyclopentadec-5-en-1-one with 3-methyl-cyclopentadec-4-en-1-one, which contain at least 70% of the former, turned out to be particularly advantageous perfuming ingredients according to the invention, since, while preserving the desired olfactive characteristics, they could be obtained in a more economic way than 3-methyl-cyclopentadec-5-en-1-one, or its isomers, in a pure state. Such mixtures are novel compositions which are also the object of the invention. Preferred mixtures of the invention contain at least 30% by weight of 3-methyl-cydopentadec-5-en-1-one in the form of its cis-configuration isomer. In the following application examples, whenever there is a reference to 3-methyl-cyclopentadec-5-en-1-one, it is also meant to refer to both its cis transisomers in a pure state and to any mixture of these isomers, or yet to the above-mentioned mixtures according to the invention.

The proportions in which these compounds can be used depend on the fragrance effect that one desires to achieve, as well as on the nature of the other perfuming co-ingredients in a given composition. By way of example, one can cite concentrations of the order of 5 to 10%, or even 20% or more by weight, relative to the weight of the perfuming composition or perfume into which they are incorporated.

When using these compounds for perfuming functional products such as soaps, shower or bath gels, shampoos or other hair-care products, cosmetic preparations, body or ambient air deodorants, detergents or fabric softeners, or household products, much lower concentrations will generally be used.

The compounds and mixtures according to the invention were prepared as follows.

In a three-neck flask equipped with pumice, a water separator, a condenser and a thermometer, were placed 1170.9 g of 14-methyl-16-oxabicyclo[10.3.1]hexadec-1(15)-ene (prepared 2900 ml of toluene. The mixture was heated to 130° to reflux the toluene through the water separator. Once all the water was eliminated, there were added 57.5 g of 85% phosphoric acid. The reaction mixture was heated during 5½ h under vigorous stirring. It was washed with water, then with 10% sodium carbonate. Concentration and distillation on residue yielded 1013 g (yield: 86,5%) of a mixture containing 40.7% by weight of (E)-3-methyl-cyclopentadec-5-en-1-one, 31.2% by weight of (Z)-3-methyl-cyclopentadec-5-en-1-one, 13.8% by weight of (E)-3-methyl-cyclopentadec-4-en-1-one and 1.5% by weight of (Z)-3-methyl-cyclopentadec-4-en-1-one, as well as minor amounts of other non-interesting isomers.

By subjecting this mixture to repeated chromatographic separations on silica gel and silica gel/AgNO$_3$ columns, using as eluting agents toluene or hexane containing from 1 to 5% ethyl acetate, there were obtained, after distillation (B.p. about 100° C./6.7Pa), the following compounds:

(E)-3-methyl-cyclopentadec-5-en-1-one (96% pure)
IR(Liq.): 1710(C=O),970(CH=CH,trans) cm$^{-1}$NMR($^1$H,360 MHz): 0.93(d,J=5.7 Hz,3H) δ ppm NMR($^{13}$C): 212(s,C=O); 132.7/129.6(2d,CH=CH);49.2/41.5(2t,CH$_2$COCH$_2$); 39.8/31.5(2t,CH$_2$C=CCH$_2$);28.4(d,CH) δ ppm MS: 236(M+,7), 178(7), 95(58), 82(62), 81(100), 69(45), 68(82), 67(81), 55(85), 47(75)

(Z)-3-methyl-cyclopentadec-5-en-1-one
IR(Liq.): 1710(C=O),about 700 (CH=CH, cis) cm$^{-1}$ NMR($^1$H,360 MHz): 1.00(d,J=7.8 Hz,3H) δ ppm NMR($^{13}$C): 211.6(s, C=O); 132.0/127.1(2d, CH=CH); 49.4/42.4(2t, CH$_2$COCH$_2$);33.5/26.2(2t,CH$_2$C=CCH$_2$);29.7(d,CH)

δ ppm MS: 236(M+, 8), 178(6), 95(43), 81(63), 79(40), 69(47), 68(87), 67(100), 55(79), 41(92)

The invention will now be described in further detail by way of the following examples.

EXAMPLE 1

Preparation of a perfuming composition

A base perfuming composition was prepared by admixing the following ingredients:

| Ingredients | Parts by weight |
| --- | --- |
| Linalyl acetate | 800 |
| Styrallyl acetate | 50 |
| Vetyveryl acetate dist. | 300 |
| Hexylcinnamic aldehyde | 500 |
| 10%* Undecylenic aldehyde | 200 |
| Bergamot essential oil | 400 |
| Eugenol | 400 |
| Hydroxycitronellol | 1000 |
| Iralia ®[1)] | 1200 |
| Iso E super ®[2)] | 300 |
| Jasmin absolute | 250 |
| Linalol | 400 |
| Phenethylol | 800 |
| Polysantol ®[3)] | 100 |
| Wardia ®[4)] | 200 |
| Benzyl salicylate | 1500 |
| Terpineol | 200 |
| Yland essential oil | 400 |
| Total | 9000 |

*in dipropylene glycol
[1)]methylionone; origin: Firmenich SA, Geneva, Switzerland
[2)]2-acetyl-1,2,3,4,6,7,8-octahydro-2,3,8,8-tetramethyl-naphthalene; origin: Int. Flavors and Fragrances Inc., USA
[3)](1'R,E)-3,3-dimethyl-5-(2',2',3'-trimethyl-3'-cyclopenten-1'-yl)-4-penten-2-ol; origin: Firmenich SA, Geneva, Switzerland
[4)]rose type composition; origin: Firmenich SA, Geneva, Switzerland When 1000 parts by weight of 3-methyl-cyclopentadec-5-en-1-one were added to this base composition of the floral, spicy type, a novel composition was obtained, the odor of which had acquired a distinct musky-sweet character, reminiscent of the odor of musk ketone. The fragrance effect thus obtained was quite similar to that achieved precisely when 1000 parts by weight of said musk ketone were added to the base composition, with however the difference that the compound of the invention imparted to the composition a more floral character.

Upon replacing 3-methyl-cyclopentadec-5-en-1-one by the same amount of one of the musky type commercial products, such as Astrotone ® (see S. Arctander, op. cit., sect. 1214), Exaltolide ® (pentadecanolide; origin: Firmenich SA, Geneva, Switzerland), Galaxolide ® (1,3,4,6,7,8-hexahydro -4,6,6,7,8,8-hexamethyl-cyclopenta-γ-2-benzopyran; origin: International Flavors & Fragrances, USA), muscone, civettone (cycloheptadecenone; origin: Firmenich SA, Geneva, Switzerland) or Tonalid ® (7-acetyl -1,1,3,4,4,6-hexamethyltetralin; origin: PFW, Holland), there was certainly obtained every time a composition with a musky character, but whose odor note was totally devoid of the nitro-musk type character, i.e. sweet, powdery and almost vanilla-like, that one obtains with either musk ketone or with 3-methyl-cyclopentadec-5-en-1-one according to the invention.

EXAMPLE 2

Preparation of a perfumed powder detergent

To a non-perfumed powder detergent there was added 0.1% of each of the following compounds to prepare 4 samples of perfumed detergent:

| Compound | Sample |
| --- | --- |
| (Z)-3-methyl-cyclopentadec-5-en-1-one | A |
| (E)-3-methyl-cyclopentadec-5-en-1-one | B |
| (Z)-3-methyl-cyclopentadec-4-en-1-one | C |
| (E)-3-methyl-cyclopentadec-4-en-1-one | D |

Four standard batches of textiles were then washed separately with respectively samples A to D. After the wash, the four textile batches were evaluated on a blind test by a panel of expert perfumers. According to the latter, the fabrics washed with samples C and D developed a very weak and classical musky type odor, while the fabrics washed with samples A and B developed a fragrance which was both floral and of the nitro-musk type, very strong and which lingered on the fabric for a long time.

EXAMPLES 3–12

The articles mentioned hereinafter were perfumed by addition of 3-methyl-cyclopentadec-5-en-1-one, in the concentrations indicated, to the non-perfumed appropriate bases.

| | Article | Conc. (% by weight) | Odor/Aspect [25° C.] | Odor/aspect [40° C.] |
| --- | --- | --- | --- | --- |
| 3. | Alcoholic cologne (95° alcohol) | 5.0 | S/N | S/N |
| 4. | Cream oil/water | 0.4 | S/N | S/N |
| 5. | Cream water/oil | 0.4 | S/N | S/N |
| 6. | Shampoo | 0.5 | S/N | S/N |
| 7. | Deodorant (spray) | 1.3 | S/N | S/N |
| 8. | Hair spray | 0.2 | S/N | S/N |
| 9. | Soap (tallow + coconut oil) | 0.5 | S/N | S/N |
| 10. | Talc | 0.5 | S/N | A/N |
| 11. | Powder detergent | 0.2 | S/N | S/N |
| 12. | Antiperspirant roll-on | 0.5 | S/N | S/N |

Key to the abbreviations:
S = stable
N = normal
A = acceptable

The perfuming and stability tests summarized in the table above showed that 3-methyl-cyclopentadec-5-en-1-one is perfectly convenient for perfuming a large variety of consumer products, thus finding a wide use in perfumery.

It was observed that it was quite efficient in covering the odor of the base, when necessary, and that it imparted to these articles a very pleasant musky, sweet and floral odor.

What we claim is:

1. A method to confer, improve, enhance or modify the odor properties of a perfuming composition or a perfumed article, which method comprises adding to said composition or article a fragrance effective amount of essentially pure 3-methyl-cyclopentadec-5-en-1-one to impart said composition or article a nitromusk-type odor character.

2. A method according to claim 1, wherein said 3-methyl-cyclopentadec-5-en-1-one is added in its trans-configuration form to impart a nitromusk and ambrette seeds type odor character.

3. A perfuming composition or a perfumed article produced by the method according to claim 1.

4. A perfuming composition or a perfumed article produced by the method according to claim 2.

5. A method to confer, improve, enhance or modify the odor properties of a perfuming composition or a perfumed article, which method comprises adding to said composition or article a fragrance effective amount of a mixture of 3-methyl-cyclopentadec-5-en-1-one and 3-methyl-cyclopentadec-4-en-1one, wherein the weight proportion of 3-methyl-cyclopentadec-5-en-1-one is equal to about 70% or more to impart to said composition or article a nitromusk-type odor character.

6. A method according to claim 5, wherein at least about 30% of the amount of said 3-methyl-cyclopentadec-5-en-1-one is added as the cis-isomer.

7. A perfuming composition or a perfumed article produced by the method according to claim 5.

8. A perfumed article according to claim 3, in the form of a perfume or cologne, a soap, a bath or shower gel, a shampoo or other hair-care product, a cosmetic preparation, a body or ambient air deodorant, a detergent or a fabric softener, or a household product.

9. A perfuming article according to claim 7, in the form of a perfume or cologne, a soap, a bath or shower gel, a shampoo or other hair-care product, a cosmetic preparation, a body or ambient air deodorant, a detergent or a fabric softener, or a household product.

10. A method to confer, improve, enhance or modify the odor properties of a perfuming composition or a perfumed article, which method comprises adding to said composition or article a fragrance effective amount of a mixture of 3-methyl-cyclopentadec-5-en-1-one and 3-methyl-cyclopentadec-4-en-1-one, wherein 3-methyl-cyclopentadec-5-en-1-one is the predominant component, to impart to said composition or article a nitromusk-type odor character.

11. A perfuming composition or a perfumed article produced by the method according to claim 6.

12. A perfumed article according to claim 11, in the form of a perfume or cologne, a soap, a bath or shower gel, a shampoo or other hair-care product, a cosmetic preparation, a body or ambient air deodorant, a detergent or a fabric softener, or a household product.

13. A perfuming composition or a perfumed article produced by the method according to claim 10.

14. A perfumed article according to claim 13, in the form of a perfume or a cologne, a soap, a bath or shower gel, a shampoo or other hair-care product, a cosmetic preparation, a body or ambient air deodorant, a detergent or a fabric softener, or a household product.

* * * * *